(12) United States Patent
Burnier

(10) Patent No.: US 6,303,656 B1
(45) Date of Patent: Oct. 16, 2001

(54) COMPOSITION COMPRISING UREA, AND ITS USES IN THE FIELD OF COSMETICS AND/OR DERMATOLOGY

(75) Inventor: Veronique Burnier, Chatellerault (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/389,325

(22) Filed: Sep. 3, 1999

(30) Foreign Application Priority Data

Sep. 9, 1998 (FR) .................................................... 9811262

(51) Int. Cl.⁷ ........................ A61K 31/17; A61K 31/535; A61K 31/045
(52) U.S. Cl. ........................ 514/588; 514/238.2; 514/727
(58) Field of Search ................................. 514/588, 238.2, 514/727

(56) References Cited

U.S. PATENT DOCUMENTS

| | | | |
|---|---|---|---|
| 4,378,430 * | 3/1983 | Modrovich .............................. | 435/12 |
| 4,745,071 * | 5/1988 | Lapicola et al. ....................... | 436/63 |
| 4,793,992 * | 12/1988 | Mathews et al. ..................... | 424/538 |
| 5,256,660 * | 10/1993 | Swan .................................. | 514/238.8 |
| 5,834,513 * | 11/1998 | Ptchelintsev et al. ................ | 514/561 |
| 6,114,337 * | 9/2000 | Pugliese et al. ...................... | 514/255 |

FOREIGN PATENT DOCUMENTS

| | | |
|---|---|---|
| 281 751 | 8/1990 | (DK) . |
| 0 499 229 | 8/1992 | (EP) . |
| 60185708 * | 9/1985 | (JP) . |
| 04081567 * | 12/1992 | (JP) . |

OTHER PUBLICATIONS

Chrisita Ackerman et al., "Percutaneous Absorption of Urea", Chemical Abstracts, vol. 105, No. 4, Abstract No. 29780b, p. 363, Jul. 28, 1986.

Database WPI, Week 8544, Derwent Publications Ltd., London, GB, AN 85–273407 and JP 60 185757, Sep. 21, 1985.

Database WPI, Week 8544, Derwent Publications Ltd., London, GB, AN 85–273384 and JP 60 185708, Sep. 21, 1985.

Database WPI, Week 8838, Derwent Publications Ltd., London, GB, AN 88–267491 and JP 63 194725, Aug. 11, 1988.

Database WPI, Week 7624, Derwent Publications Ltd., London, GB, AN 76–44587x and JP 51 048441, Apr. 26, 1976.

Yanagida et al, Skin cosmetics containing urea and taurine, abstract JP 60185708 & JP 04081567: CAPLUS database, 1985 & 1992.*

* cited by examiner

Primary Examiner—Marianne M. Cintins
Assistant Examiner—Vickie Kim
(74) Attorney, Agent, or Firm—Oblon, Spivak, McClelland, Maier & Neustadt, P.C.

(57) ABSTRACT

A composition comprising urea and an N-substituted aminosulfonic acid. The composition may be used for the care, treatment and/or protection of human skin, mucous membranes and/or keratin fibers, in particular for moisturizing the skin and for the treatment of dry skin.

17 Claims, No Drawings

COMPOSITION COMPRISING UREA, AND ITS USES IN THE FIELD OF COSMETICS AND/OR DERMATOLOGY

BACKGROUND OF THE INVENTION

1. Field of the Invention

The present invention relates to a composition which stably comprises urea and which is intended, in particular, for use in the fields of cosmetics and/or dermatology. The invention also relates to a use of this composition for the care, the treatment, the protection and/or hydration of human skin, of mucous membranes and/or keratin fibers, and for the treatment of dry skin.

2. Discussion of the Background

In cosmetic or dermatological compositions, moisturizers, i.e., hygroscopic substances which allow the water content in the skin to be retained and thus the suppleness and the touch of the skin to be affected advantageously, are widely used. Such moisturizers are also useful for hydrating the skin and, in particular for treating dry skin.

Among the many moisturizers, urea is particularly important. Urea is a component of the NMF (natural moisturizer factor) and has a softening effect on the corneal layers of the skin.

However, the disadvantage of urea is that it is generally not stable in an aqueous environment, where it degrades into carbon dioxide and ammonia. This leads to a rise in pH of the composition containing it and the release of an odor, which make the use of such compositions very unsatisfactory.

It has therefore been attempted for a long time to formulate urea in cosmetically acceptable compositions in a form which is stable over at least several months. Thus, document JP51048441 describes the stabilization of urea in a glycine/sodium hydroxide buffer at a pH of 6 to 9. However, the use of such a buffer has the disadvantage of making the composition containing it sticky when applied to the skin.

Accordingly, there remains therefore the need for stable urea-based compositions which have satisfactory cosmetic properties.

SUMMARY OF THE INVENTION

It is an object of the invention to provide a stable moisturizing composition contains urea.

It is another object of the present invention to provide a moisturizing composition which contains urea and water.

It is another object of the present invention to provide a method of moisturizing skin with a composition containing urea.

In a surprising and unexpected manner, the Inventor has discovered that it is possible to formulate compositions which comprise urea and which are stable over time and pleasant to use, by using an N-substituted aminosulfonic acid.

Accordingly, the objects of the invention, and others, may be accomplished with a composition comprising urea and at least one N-substituted aminosulfonic acid.

The objects of the invention may also be accomplished with a method of treating body skin and/or facial skin, comprising applying the composition to body skin and/or facial skin.

The objects of the invention may also be accomplished with a method of treating dry skin, comprising applying the composition to dry skin.

The objects of the invention may also be accomplished with a method of moisturizing skin comprising applying a composition comprising urea and at least one N-substituted aminosulfonic acid to dry skin.

The objects of the invention may also be accomplished with a method of preparing the inventive composition comprising combining urea and at least one N-substituted aminosulfonic acid.

An advantage of the composition according to the invention is that it can comprise stable urea after storage at 45° C. over 2 months. Another advantage of the composition according to the invention is that it is particularly well tolerated by the skin and the keratin fibers and that it is extremely suitable for a topical use, in particular a cosmetic and/or dermatological use.

A more complete appreciation of the invention and many of the attendant advantages thereof will be readily obtained as the same becomes better understood by reference to the following detailed description.

DETAILED DESCRIPTION OF THE INVENTION

The N-substituted aminosulfonic acid of the inventive composition generally constitutes a buffer with a pKa at approximately 20° C. ranging from 6 to 7.8, preferably 6.3 to 7.6. These ranges include all specific pHs and subranges therebetween, such as 6.1, 6.2, 6.4, 6.5, 6.8, 7.0, 7.2 and 7.5.

The N-substituted aminosulfonic acid can be chosen, in a preferred embodiment, from the amino derivatives of alkylsulfonic acids, where the alkyl group preferably has 1 to 6 carbon atoms, more preferably 2 to 3 carbon atoms. Amino derivatives of ethanesulfonic acid and propanesulfonic acid are particularly preferred.

Specific examples of N-substituted aminosulfonic acids include are N,N-bis[2-hydroxyethyl]-2-aminoethanesulfonic acid (pKa=7.17), N-2-hydroxyethylpiperazine-N'-2-ethanesulfonic acid (pKa=7.55), 3-[N-morpholino]propanesulfonic acid (pKa=7.15), piperazine-N,N'-bis[2-ethanesulfonic] acid (pKa=6.82), 3-[N-tris(hydroxymethyl)methylamino]-2-hydroxypropanesulfonic acid (pKa=7.6), 2-[N-morpholino]ethanesulfonic acid (pKa=6.15), N-(2-acetamido)-2-aminoethanesulfonic acid (pKa=6.88), N-tris(hydroxymethyl)methyl-2-aminoethanesulfonic acid (pKa=7.5). A mixture of these acids may also be used. The pKa values given hereinabove are those determined at approximately 20° C. at a concentration of 0.1 M.

The quantity of N-substituted aminosulfonic acid(s) is preferably high enough to achieve the intended result, i.e., stabilization of the urea in the composition. This quantity may range, for example, from 0.1 to 20% by weight, preferably 0.5 to 15% by weight, based on the total weight of the composition. These ranges include all specific values and subranges therebetween, such as 0.2, 1, 2, 5, 8, 10, 12 and 18% by weight.

The quantity of urea in the composition may vary within a wide range. For a cosmetic and/or dermatological application, the urea is preferably present in a quantity which generally ranges from 0.1 to 20% by weight, preferably 0.5 to 15% by weight, based on the total weight of the composition. These ranges include all specific valves and subranges therebetween, such as 0.2, 1, 2, 5, 8, 10, 12 and 18% by weight.

In a preferred embodiment, the inventive composition contains water. The amount of water in the composition may vary widely. For example, the composition may contain 0.5 to 99.5% water by weight, based on the total weight of the composition. This range includes all specific values and subranges therebetween, such as 1, 2, 5, 10, 20, 25, 30, 40, 50, 60, 70, 80, 90, 95, 98, and 99% by weight, based on the total weight of the composition.

The composition preferably has a pH of approximately 7 to ensure better stability of the urea. By a pH of approximately 7 there is understood a pH which ranges from 6.5 to 7.5. The pH of the composition preferably ranges from 6.8 to 7.2. The pH may be adjusted by any suitable means which is known and, depending on the circumstances, by an inorganic acid or organic acid such as hydrochloric acid or citric acid, or an inorganic or organic base, such as sodium hydroxide and triethanolamine. Depending on the pH, the N-substituted aminosulfonic acid can be in partial salt form.

It is known that urea undergoes less degradation when the composition comprising it has a pH of 7. However, even at this pH, an unavoidable degradation takes place over time. In the composition according to the invention, the degradation of urea is avoided owing to the presence of the N-substituted aminosulfonic acid.

The composition of the invention may be, in a preferred embodiment, a cosmetic or dermatological composition, and thus comprises a physiologically acceptable carrier, i.e., one that is compatible with the skin, the mucous membranes, including lips and/or the keratin fibers (hair, eyelashes). This composition may be present in any pharmaceutical form for topical use which are normally employed, for example, in the form of an aqueous or oily solution, an aqueous or oily suspension or a dispersion of the lotion or serum type, or emulsions obtained by dispersing a fatty phase in an aqueous phase (O/W) or the other way round (W/O), triple emulsions (W/O/W or O/W/O) or ionic and/or nonionic vesicle dispersions. These compositions may be prepared by well-known methods. According to a preferred embodiment of the invention, the composition is in the form of an O/W emulsion.

The quantities of the different constituents of the compositions are those which are customarily used in the field of skin treatments, which are well-known to those skilled in the art.

When the composition is an emulsion, the amount of fatty phase may range from 5 to 80% by weight, preferably 5 to 50% by weight, based on the total weight of the composition. These ranges included all specific values and subranges thereafter, such as 10, 20, 30, 40, 60 and 70% by weight. The oils, waxes, emulsifiers and coemulsifiers used in the composition in the form of an emulsion are selected from amongst those conventionally used in the fields of cosmetics and dermatology. The emulsifier and coemulsifier are present in the composition in amounts of preferably 0.3 to 30% by weight, more preferably 0.5 to 20% by weight, based on the total weight of the composition. The emulsion may additionally comprise lipid vesicles.

Oils or waxes which may be used in the invention and which may be mentioned are mineral oils (liquid petrolatum), vegetable oils (liquid fraction of shea butter, sunflower oil), animal oils (perhydrosqualene), synthetic oils (isopropyl myristate), silicone oils or waxes (cyclomethicone) and fluorinated oils (perfluoropolyethers), beeswax, carnauba wax or paraffin wax. Fatty alcohols (cetyl alcohol) and fatty acids (stearic acid) may be added to these oils.

Examples of emulsifiers which can be used in the invention include glycerol stearate and PEG-50 stearate.

The cosmetic or dermatological composition may also comprise, in a known manner, the adjuvants conventionally used in the field of cosmetics or dermatology such as hydrophilic or lipophilic gellants, hydrophilic or lipophilic additives, preservatives, antioxidants, solvents, fragrances, fillers, sunscreens, odor absorbers and colorants. The quantities of these various adjuvants are those conventionally used in these fields, for example from 0.01 to 10% of the total weight of the composition. These ranges included all specific valves and subranges thereafter, such as 0.02, 0.05, 1, 2, 3, 5 and 8% by weight. Depending on their nature, these adjuvants may be introduced into the fatty phase, the aqueous phase and/or into lipid spherules.

Hydrophilic gellants which can be used in the invention and which may be mentioned are the carboxyvinyl polymers (carbomer), acrylic copolymers such as acrylate/alkyl acrylate copolymers, polyacrylamides, polysaccharides such as hydroxypropyl cellulose, natural gums, clays, and, as lipophilic gellants there may be mentioned modified clays such as bentonites and metal salts of fatty acids such as aluminium stearates.

As long as they do not interfere with the urea, the compositions according to the invention may comprise other active materials. Particularly preferred additional active materials are those for the prevention and/or treatment of skin ailments.

Examples of other active materials include polyols such as glycerol, glycols and sugar derivatives, enzymes, vitamins such as vitamin C (ascorbic acid), vitamin A (retinol), vitamin D, vitamin E (tocopherol), vitamin K and the derivatives of these vitamins such as esters, ceramides, pigmentation-reducing agents such as kojic acid and caffeic acid, beta-hydroxy acids such as salicylic acid and its derivatives, alpha-hydroxy acids such as lactic acid and glycolic acid, moisturizers such as protein hydrolysates, softeners such as allantoin, and mixtures thereof.

The compositions of the invention are especially useful for the care, treatment and/or protection of the skin of the face and/or the body, and in particular for moisturizing the skin. Accordingly, the present invention includes the use of the composition described above for the care, treatment, protection and/or for moisturizing the skin of the face and/or the body.

Owing to the moisturizing properties of urea, the composition according to the invention can be used for the dermatological treatment of dry skin.

The invention therefore also relates to the use of the composition defined hereinabove for the preparation of a dermatological composition intended for the treatment of dry skin.

For each of the uses described above, the composition may be applied to the area to be treated. The composition may be topically applied using a conventional topical applicator device, e.g., a cloth, pad or brush. Alternatively, the composition may be rubbed over the area to be treated with the fingers.

Having generally described this invention, a further understanding can be obtained by reference to certain specific examples which are provided herein for purposes of illustration only and are not intended to be limiting unless otherwise specified.

EXAMPLES

The quantities given in the compositions are percentages by weight, based on the total weight of the composition.

Example 1
O/W Emulsion

| Oily phase | |
|---|---|
| Cetyl alcohol | 7% |
| Glyceryl stearate | 2.5% |
| PEG-50 stearate | 2.5% |
| Petrolatum oil | 6.2% |
| Isopropyl myristate | 3% |
| Aqueous phase | |
| Preservatives | 0.3% |
| Urea | 10% |
| 3-[N-morpholino]propanesulfonic acid | 7% |
| Sodium hydroxide | q.s. pH = 7 ± 0.2 |
| Water | q.s. 100% |

Procedure: the oily phase is heated to 80° C. Separately, some of the water of the aqueous phase and the preservative are mixed and the mixture is heated to 80° C., and the oily phase is then introduced into the aqueous phase with stirring. The emulsion obtained is cooled to a temperature of approximately 40° C., and 3-[N-morpholino] propanesulfonic acid, solubilized in a small amount of water, is added: the pH is adjusted with sodium hydroxide and the urea, which has been solubilized in a small amount of water, is introduced into the emulsion. The pH is again adjusted to approximately 7.

After 2 months at 45° C., the urea concentration in the composition has remained the same, the pH has not risen beyond 0.4 units, that is to say a variation of +5.6%, and the stored composition does not release any odor, while in an identical composition without aminosulfonic acid, the urea concentration has dropped 13% after 2 months at 45° C., the pH has risen by 1.8 units, that is to say a variation of +27%, and the composition has the odor of ammonia.

The emulsion obtained has good cosmetic properties (is not sticky) and is suitable for treating the skin with the purpose of moisturizing the skin while making it softer.

Example 2
O/W Emulsion

| Oily phase | |
|---|---|
| Cetyl alcohol | 7% |
| Glyceryl stearate | 2.5% |
| PEG-50 stearate | 2.5% |
| Petrolatum oil | 6.2% |
| Isopropyl myristate | 3% |
| Aqueous phase: | |
| Urea | 10% |
| Piperazine-N,N'-bis[2-ethanesulfonic] acid | 10% |
| Preservatives | 0.3% |
| Sodium hydroxide | q.s. pH = 7 ± 0.2 |
| Water | q.s. 100% |

The procedure is the same as in Example 1.

After 2 months at 45° C., the urea concentration has dropped by only 5.7%, the pH has only risen by 0.7 units, that is to say a variation of +10%, and the composition does not release any odor, while in an identical composition without aminosulfonic acid, the urea concentration has dropped by 13% after 2 months at 45° C., the pH has risen by 1.8 units, that is to say a variation of +27%, and the composition has the odor of ammonia.

The emulsion obtained has good cosmetic properties (is not sticky) and is suitable for treating the skin with the purpose of moisturizing the skin while making it softer.

Example 3
O/W Emulsion

| Oily phase | |
|---|---|
| Cetyl alcohol | 7% |
| Glyceryl stearate | 2.5% |
| PEG-50 stearate | 2.5% |
| Petrolatum oil | 6.2% |
| Isopropyl myristate | 3% |
| Aqueous phase | |
| Urea | 10% |
| N,N'-bis[2-Hydroxyethyl]-2-aminoethane sulfonic acid | 7.1% |
| Preservatives | 0.3% |
| Sodium hydroxide | q.s. pH = 7 ± 0.2 |
| Water | q.s. 100% |

The procedure is the same as in Example 1.

After 2 months at 45° C., the urea concentration has dropped by only 7.6%, the pH has only risen by 0.7 units, that is to say a variation of +10%, and the composition does not release any odor, while in an identical composition without aminosulfonic acid, the urea concentration has dropped by 13% after 2 months at 45° C., the pH has risen by 1.8 units, that is to say a variation of +27%, and the composition has the odor of ammonia.

The emulsion obtained has good cosmetic properties (is not sticky) and is suitable for treating the skin with the purpose of moisturizing the skin while making it softer.

Obviously, numerous modifications and variations of the present invention are possible in light of the above teachings. It is therefore to be understood that within the scope of the appended claims, the invention may be practiced otherwise than as specifically described herein.

This application is based on French Application Serial No. 98-11262, filed on Sep. 9, 1998, and incorporated herein by reference.

What is claimed is:

1. A composition in the form an emulsion, comprising urea and an effective urea-stabilizing amount of at least one N-substituted aminosulfonic acid, wherein the N-substituted aminosulfonic acid has a pKa at approximately 20° C. of 6 to 7.8.

2. The composition of claim 1, which has a pH of 6.5 to 7.5.

3. The composition of claim 1, wherein the N-substituted aminosulfonic acid has a pKa at approximately 20° C. of 6.3 to 7.6.

4. The composition of claim 1, wherein the N-substituted aminosulfonic acid is selected from the group consisting of the amino derivatives of alkylsulfonic acids.

5. The composition of claim 1, wherein the N-substituted aminosulfonic acid is selected from the group consisting of the amino derivatives of alkylsulfonic acids, wherein the alkyl group comprising 1 to 6 carbon atoms.

6. The composition of claim 1, wherein the N-substituted aminosulfonic acid is selected from the group consisting of N,N-bis[2-hydroxyethyl]-2-aminoethanesulfonic acid, N-2-hydroxyethylpiperazine-N'-2-ethanesulfonic acid, 3-[N-morpholino]propanesulfonic acid, piperazine-N,N'-bis[2-ethanesulfonic] acid, 3-[N-tris(hydroxymethyl) methylamino]-2-hydroxypropane-sulfonic acid, 2-[N-morpholino]ethanesulfonic acid, N-(2-acetamido)-2-aminoethanesulfonic acid, N-tris-(hydroxymethyl)methyl-2-aminoethanesulfonic acid, and mixtures thereof.

7. The composition of claim 1, wherein the amount of N-substituted aminosulfonic acid(s) in the composition is 0.1 to 20% by weight, based on the total weight of the composition.

8. The composition of claim 1, wherein the amount of N-substituted aminosulfonic acid(s) in the composition is from 0.5 to 15% by weight, based on the total weight of the composition.

9. The composition of claim 1, comprising 0.1 to 20% by weight of the urea, based on the total weight of the composition.

10. The composition of claim 1, comprising 0.5 to 15% by weight of the urea, based on the total weight of the composition.

11. The composition of claim 1, which is suitable for topical application to human skin.

12. The composition of claim 1, which is in the form of an O/W emulsion.

13. The composition of claim 1, comprising 0.5 to 99.5 wt. % water, based on the total weight of the composition.

14. A method of treating body skin and/or facial skin, comprising applying the composition of claim 1 to body skin and/or facial skin.

15. A method of treating dry skin, comprising applying the composition of claim 1 to dry skin.

16. A method of preparing the composition of claim 1 comprising combining the urea and the N-substituted aminosulfonic acid.

17. A method of stabilizing a composition in the form of an emulsion, containing urea, comprising incorporating at least one N-substituted aminosulfonic acid into the composition, wherein the N-substituted aminosulfonic acid has a pKa at approximately 20° C. of 6 to 7.8.

* * * * *

UNITED STATES PATENT AND TRADEMARK OFFICE
CERTIFICATE OF CORRECTION

PATENT NO.    : 6,303,656 B1
DATED         : October 16, 2001
INVENTOR(S)   : Veronique Burnier It is certified that error appears in the above-identified patent and that said Letters Patent is hereby corrected as shown below:

<u>Column 6,</u>
Line 38, "form an emulsion" should read -- form of an emulsion --.

Signed and Sealed this

Second Day of April, 2002

Attest:

Attesting Officer

JAMES E. ROGAN
Director of the United States Patent and Trademark Office